United States Patent [19]

Drennen

[11] Patent Number: 5,492,314
[45] Date of Patent: Feb. 20, 1996

[54] PRELOADED DIGRESSIVE RATE MOUNT

[75] Inventor: David B. Drennen, Bellbrook, Ohio

[73] Assignee: General Motors Corporation, Detroit, Mich.

[21] Appl. No.: 398,833

[22] Filed: Mar. 6, 1995

[51] Int. Cl.[6] .................. B60G 7/02; F16F 3/08
[52] U.S. Cl. .................... 267/220; 267/140.2
[58] Field of Search ............ 267/33, 35, 64.15, 267/153, 140.2, 140.4, 141.1, 141.2, 219, 220, 221; 280/668, 671, 688, 716

[56] References Cited

U.S. PATENT DOCUMENTS

| | | | |
|---|---|---|---|
| 3,954,255 | 5/1976 | Keijzev et al. | 267/220 |
| 4,175,771 | 11/1979 | Muzechuk et al. | 267/220 |
| 4,434,977 | 3/1984 | Chiba et al. | 267/220 |
| 4,568,067 | 2/1986 | Iwata | 267/33 |
| 4,618,127 | 10/1986 | Le Salvev et al. | 247/220 |
| 4,711,463 | 12/1987 | Knable et al. | 280/668 |
| 4,810,003 | 3/1989 | Pinch et al. | 267/33 |
| 5,150,886 | 9/1992 | Hamberg et al. | 267/220 |
| 5,186,440 | 2/1993 | Schobbe et al. | 267/33 |
| 5,211,380 | 5/1993 | Germano | 267/220 |
| 5,259,600 | 11/1993 | de Fontenay et al. | 267/220 |
| 5,263,694 | 11/1993 | Smith et al. | 267/220 |

FOREIGN PATENT DOCUMENTS

| | | | |
|---|---|---|---|
| 3532681 | 3/1987 | Germany | 280/668 |
| 4358916 | 12/1992 | Japan | 267/220 |

*Primary Examiner*—Robert J. Oberleitner
*Assistant Examiner*—Chris Schwartz
*Attorney, Agent, or Firm*—Jeffrey A. Sedlar

[57] ABSTRACT

A top hydro-pneumatic suspension mount is embodied in a single path preloaded shear compression arrangement achieved by positioning a rate plate between the upper jounce plate and the molding assembly thereby providing a digressive rate performance concurrently providing stiff performance for supporting the vehicle and resilient performance for isolating vertical road input loads.

5 Claims, 1 Drawing Sheet

5,492,314

PRELOADED DIGRESSIVE RATE MOUNT

BACKGROUND OF THE INVENTION

The present invention relates to mounts for suspension actuators and dampers and more particularly, to top mounts for a hydro-pneumatic struts.

A typical top mount secures the upper end of a suspension actuator or damper to a body. Conventional top mounts include at least one resilient element (rubber cushion), to isolate and reduce the transmission of input forces to the body. A top mount is generally required to be firm enough to support the weight of the body while simultaneously resilient enough for isolation purposes. For certain inputs deflection of the top mount is desirable while for other inputs it is preferable for the top mount to resist deflection.

Single path top mounts are known, wherein the actuator or damper rod and a coil spring seat are fastened together and the load path is through a single rubber cushion. The single rubber cushion accommodates the forces generated by both the actuator or damper and the cooperating coil spring. The rubber cushion is preloaded by the vehicle's weight and therefore, compression set of the rubber cushion becomes a concern. It is also known that such single path mounts may exhibit inadequate tunability features.

Dual path mounts are known, wherein the actuator or damper rod and the coil spring seat are not fastened together and wherein the load path is through separate rubber cushion assemblies. A first rubber cushion assembly engages the coil spring and supports the vehicle's weight and the second rubber cushion assembly engages the actuator or damper rod and is not preloaded by vehicle weight. These dual path mounts exhibit somewhat improved tunability over conventional single path mounts but may provide a compromised spring rate to accommodate the two different forces.

With the described single and dual path mounts, the coil spring supports the weight of the vehicle and creates a force that is proportional to the relative velocity between the vehicle's wheel and its body. The coil spring and actuator or damper are attached between the wheel and the body by the top mount. Therefore, the top mount must support the total weight of the vehicle and provide acceptable isolation.

Hydro-pneumatic struts are known which function as both a spring and a damper. Because there is no conventional coil spring component in a suspension incorporating hydro-pneumatic struts, the conventional dual path mount described above cannot effectively be used with a hydro-pneumatic strut. A conventional single path mount can be utilized with a hydro-pneumatic strut but due to large vehicle corner weight in the vertical direction, the conventional mount generally exceeds the current vertical space available in the strut tower area for many vehicles. Therefore, an acceptable top strut mount that fits within the available limited space of a vehicle and provides desirable performance characteristics is required.

SUMMARY OF THE INVENTION

The present invention provides a single path digressive rate top mount for use with hydro-pneumatic struts that is stiff enough to support the vehicle and resist deflection while concurrently soft enough to deflect to provide good isolation of road inputs in the vertical direction. A top mount according to the present invention is a preloaded shear compression mount. The mount includes a rate plate positioned between a molding assembly, which carries the sole resilient cushion, and the upper jounce plate, thereby applying a preload to the resilient cushion of the molding assembly. The rate plate's thickness is determined by the rubber rate of the resilient cushion and enables positioning the strut rod in a predetermined position regardless of the mount rate required for the application. A digressire rate mount is preferably provided by preloading the mount with the rate plate. The preloading restricts mount travel until a certain force is obtained thereby creating a digressive rate performance. Concurrently, the use of the rate plate permits using a relatively low durometer rubber for the resilient cushion and allows the strut rod to deflect a greater distance, i.e., a softer rate is provided, for isolating road inputs.

DETAILED DESCRIPTION OF THE PRESENTLY PREFERRED EMBODIMENT

Figure 1:
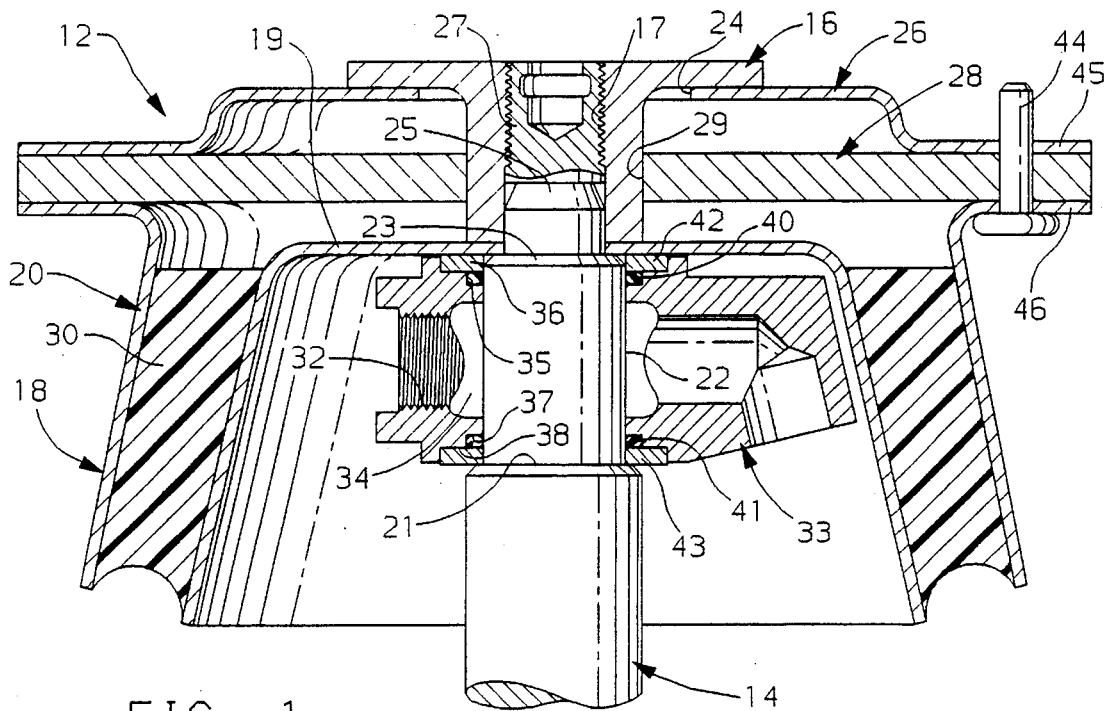
FIG. 1 is a cross-sectional view of a top front strut mount according to the present invention.

Referring to the drawings, FIG. 1 illustrates a top front strut mount 12 according to the present invention. Strut rod 14 engages strut mount 12 and includes shoulders 21, 23, and 25 and threaded portion 27. Strut rod 14 includes cylindrical section 22 which extends between shoulders 21 and 23.

Positioned around cylindrical section 22 is fitting 33. Fitting 33 includes port 32 and chamber 34 providing a means of fluid communication with the hollow interior (not illustrated) of strut rod 14. Strut rod 14 carries hydraulic fluid as is conventionally known in the hydro-pneumatic suspension art. Fitting 33 includes stepped annular grooves 35–36 and 37–38 which are coaxial with strut rod 14. Grooves 35 and 37 carry annular seals 40 and 41, respectively and grooves 36 and 38 carry washers 42 and 43, respectively. The seals 40 and 41 are retained by washers 42 and 43 and maintain the fluid pressure within chamber 34. Washer 43 engages shoulder 21 of strut rod 14 and washer 42 engages inside cup 19 of molding assembly 18.

Molding assembly 18 includes inside cup 19 and outside cup 20 which are integrally connected by resilient cushion 30 which is conventionally formed from rubber or a similar material with an adhered connection to the cups 19 and 20.

Vertical stop 16 threadedly engages threaded portion 27 of strut rod 14 and extends through opening 24 of upper jounce plate 26 and opening 29 of rate plate 28, thereby maintaining mount 12 in an assembled relationship. As the threaded portion 27 of strut rod 14 is drawn into threaded opening 17 of vertical stop 16 the outside cup 20 is displaced downward from its normal position while inside cup 19 is drawn to a predetermined consistent location thereby preloading the resilient cushion 30. The initial deflection of mount 12 is restricted to the upward direction by vertical stop 16.

Three fasteners, represented by fastener 44, extend through the outer peripheral legs 45 and 46 of upper jounce plate 26 and outside cup 20, respectively and also through rate plate 28. The fasteners serve to attach mount 12 to the upper strut tower (not illustrated) of a vehicle.

Figure 2:
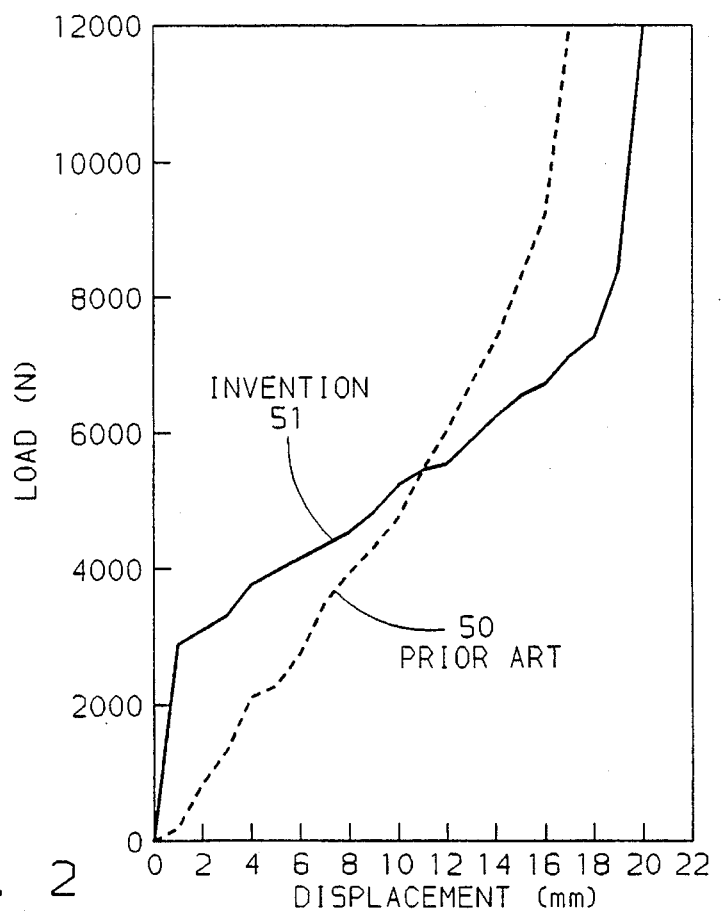
FIG. 2 is a performance curve of load versus mount displacement.

By preloading resilient cushion 30 through the positioning and selected thickness of rate plate 28, travel of mount 12 is restricted until a certain force is obtained, creating digressive rate mount curve illustrated in FIG. 2 as curve 51. Curve 50 represents the performance of a conventional single path mount without a rate plate imposed preload. Therefore, FIG. 2 illustrates that by preloading resilient cushion 30 a digressive rate performance is obtained. This is desirable to the performance of a strut mount for a hydropneumatic suspension. The resulting mount 12 is firm enough to support the vehicle's weight yet soft enough for good isolation of high load road inputs in the vertical direction.

In the present application the preferred thickness of rate plate 28 is such that the preload in resilient cushion 30 offsets the static mount deflection under a vehicle preload of approximately 6000 Newtons. Without the preload, a significantly higher durometer rubber would be needed for resilient cushion 30, effecting isolation characteristics of the mount 12.

What is claimed is:

1. A mount for attaching a suspension damper to a body comprising:

an upper jounce plate;

a molding assembly including an inner cup and an outer cup radially outside the inner cup, said cups connected together by a resilient cushion; and a rate plate interposed between the upper jounce plate and the molding assembly such that a load is established in the resilient cushion due to a displacement of the outer cup caused by the interpositioning of the rate plate.

2. The mount according to claim 1 wherein the upper jounce plate is fixed in position relative to the rate plate and the inner cup is engaged with the damper such at the inner cup is movable relative to the upper jounce plate and the rate plate.

3. The mount according to claim 1 wherein a weight load is imposed on the damper and the load established in the resilient cushion substantially equals and opposes the weight load.

4. The mount according to claim 2 further comprising a vertical stop wherein the damper fixedly engages the vertical stop and the vertical stop releasably engages the upper jounce plate such that the mount is limited to initial deflection in an upward direction wherein the inner cup initially moves relative to the upper jounce plate in the upward direction.

5. The mount according to claim 4 further comprising a damper rod extending from the damper and wherein the inner cup is captured between the damper rod and the vertical stop by the damper rod and the vertical stop.

* * * * *